United States Patent [19]

Schroeder et al.

[11] 4,260,546
[45] Apr. 7, 1981

[54] AGED MOLTEN COLOR OF MALEIC ANHYDRIDE

[75] Inventors: Hobe Schroeder, Warrenville; Donald E. Thomka, Romeoville, both of Ill.

[73] Assignee: Standard Oil Company (Indiana), Chicago, Ill.

[21] Appl. No.: 106,670

[22] Filed: Dec. 26, 1979

[51] Int. Cl.³ ............................................ C07D 307/60
[52] U.S. Cl. ................................................. 260/346.76
[58] Field of Search ....................... 260/346.76, 346.74

[56] References Cited

U.S. PATENT DOCUMENTS

| 3,564,022 | 2/1971 | Manoff et al. | 260/346.74 |
| 3,939,183 | 2/1977 | Gardner et al. | 260/346.76 |

Primary Examiner—Henry R. Jiles
Assistant Examiner—Bernard Dentz
Attorney, Agent, or Firm—Fred R. Ahlers; Wiliam T. McClain; William H. Magidson

[57] ABSTRACT

The oxidation of butane vapor with air produces an impure maleic anhydride which when fractionated to first remove materials boiling lower than maleic anhydride and then a maleic anhydride product, leads to a maleic anhydride product fraction which when held at 140° C. for 90 minutes discolors and is not a commercially acceptable product. Such discoloration can be substantially reduced by maintaining the impure maleic anhydride at a temperature from 60° up to 200° C. in the presence of small amounts of either hydrogen peroxide and/or sulfuric acid.

4 Claims, No Drawings

AGED MOLTEN COLOR OF MALEIC ANHYDRIDE

FIELD OF THE INVENTION

This invention relates to the treatment of maleic anhydride derived from air oxidation of butane whose molten color increases with time and more specifically pertains to the use of hydrogen peroxide or hydrogen peroxide and sulfuric acid as addition agents in such maleic anhydride heat treated prior to final fractionation.

BACKGROUND OF THE INVENTION

Maleic anhydride had long been manufactured by the catalytic oxidation of benzene vapor with air. The gaseous effluent from such oxidation contains mainly nitrogen and unused oxygen together with oxides of carbon, water vapor, maleic anhydride vapor, and vapors of oxygen-containing organic compounds coproduced as impurities. Such gaseous effluent is cooled to a temperature below the boiling temperature of maleic anhydride but above 100° C. to recover the anhydride as an impure liquid product. The resulting cooled gaseous mixture is scrubbed with a liquid to remove all of the maleic anhydride before venting the remaining gases and vapors. Maleic anhydride as second impure portion of product may be recovered from the scrubbing liquor and combined with the first portion of impure maleic anhydride product and then further processed at least by fractionation to recover purified maleic anhydride.

The quality specifications for commerially acceptable purified maleic anhydride include color values of molten anhydride both upon initial melting and after being held at 140° C. for 90 minutes. The initial molten color should not exceed 20 and the aged color should not exceed 40 APHA Color Values as determined and described in ASTM test method D 3366-74.

To meet the aged molten color specification, the manufacturers of maleic anhydride found it necessary to subject the impure anhydride to a heat treatment step prior to fractionation so that colored body or color-forming impurities distilling with the anhydride would be converted to higher boiling substances. Such heat treatment was effectively maintained for periods of time which became economically and productively unattractive. The heat treatment of impure maleic anhydride was shortened by conducting this partial purification step in the presence of various addition agents. Following such time shortened heat treatment the mixture was subjected to a simple distillation to remove maleic anhydride and materials boiling at a temperature below the boiling temperature of said anhydride. The resulting partially purified maleic anhydride was then subjected to fractionation to remove the low boiling impurities as a top fraction, purified maleic anhydride product as an intermediate fraction, and leave whatever higher boiling impurities not before removed or which formed during distillation or fractionation as a bottom fraction.

Now the catalytic oxidation of butane vapor with air has become an important route for the manufacture of maleic anhydride. The gaseous effluent from the oxidation also contains mainly nitrogen and unused oxygen together with oxides of carbon, water vapor, maleic anhydride vapor, and vapors of oxygen-containing organic compounds co-produced as impurities. Although those oxygen-containing organic co-products which were colored bodies or color formers differed in character and nature from such colored body and color formers in impure maleic anhydride product from the vapor phase benzene oxidation, similar heat treatment steps were successfully applied to assist in the removal of the impurities prior to or during the final fractionation purification.

Sulfuric acid, sulfur trioxide, oleum or sodium acid sulfate are taught in U.S. Pat. No. 2,296,218 as being useful as time shortening addition agents for the heat treatment partial purification of impure maleic anhydride obtained from benzene vapor oxidation. However, we found that sulfuric acid at the 0.5 weight percent concentration provided a corrosive environment as a time shortening addition agent for the partial purification of maleic anhydride obtained from butane vapor oxidation with air.

We have now found a co-additive or adjunct additive for use with sulfuric acid during the heat treatment partial purification step used prior to final fractionation which provides the sought improvement of aged molten color of maleic abhydride obtained from air oxidation of butane vapor.

STATEMENT OF THE INVENTION

We have discovered that the aged molten color of maleic anhydride product from its final fractionation can be improved provided that the impure maleic anhydride obtained from catalytic air oxidation of butane is partially purified by maintaining the impure anhydride in the liquid state in the presence of rather low concentrations of hydrogen peroxide, e.g., less than 0.1 down to 0.01 weight percent of hydrogen peroxide, and/or in the presence of sulfuric acid in a concentration below 0.5 weight percent, e.g., 0.2 weight percent or less. In addition to the beneficial effect of the use of such addition agents, there is also the benefit derived from the fact that they are both liquids and are thus easily metered into the heat treatment step. Also, hydrogen peroxide alone does not create a corrosive environment. Further, when sulfuric acid and hydrogen peroxide are used together, the low concentration of sulfuric acid, i.e., not to exceed 0.1 weight percent, does not create a corrosive environment as would the use of sulfuric acid at the prior suggested 0.5 weight percent concentration.

Generally in the large scale commercial continuous production of maleic anhydride, the impure product is held for 20 to 48 hours in the liquid state between its recovery and final fractionation. By the practice of this invention the hydrogen peroxide in a concentration of up to 0.1 weight percent, or sulfuric acid (100% $H_2SO_4$) in a concentration of up to 0.2 weight percent, or a combination of up to 0.1 weight percent hydrogen peroxide and up to 0.1 weight percent sulfuric acid (100% $H_2SO_4$ can be added to the molten anhydride as it flows from its recovery from the gaseous mixture to the hold tanks prior to the final fractionation.

The heat treatment step is to be performed before final fractionation and is performed preferably with the impure anhydride fed to the fractionator; that is, without separation from the addition agents or impurities converted by the addition agents. Temperatures for the heat treatment can be from 60° C. to 202° C. At low temperatures a long heat soak is needed. Higher temperatures have the disadvantage of rapidly decomposing maleic anhydride and hydrogen peroxide. Convenient conditions for commercial practice of the present invention comprise a temperature of 150° C. maintained for 24 hours. Both batch and continuous operations are effective. The amount of additives to be used depends on the impurity content. Minute quantities are effective. High concentrations of sulfuric acid of about 0.5% can cause corrosion problems.

EXAMPLE 1

The effect of a heat treatment with sulfuric acid as additive was evaluated in batch operations, that is both the heat treatment as well as the fractionation were done batchwise. Crude maleic anhydride for these experiments was obtained from the crude storage tank of a commercial unit wherein butane vapor is oxidized with air. A portion of the sample was fractionated without pretreatment. Another portion was subjected to a 24 hour batch heat treatment at 150° C. with the addition of 0.1 (wt)% sulfuric acid. All samples were fractionated in a 20 tray column whose trays have a separation efficiency of 50% at the conditions of 100 mm Hg absolute pressure, a 1% forecut takeoff and a 1:1 reflux ratio during heart cut takeoff. Duplicate experiments were conducted, that is, experiment 1B is a duplicate of experiment 1A. The results of said experiments are shown in TABLE I to follow wherein "IMC" is used to designate initial molten color and "AMC" is used to designate aged molten color, the APHA color rating after holding for 90 minutes at 140° C.

TABLE I $H_2SO_4$ AS HEAT TREATMENT ADDITIVE PRIOR TO BATCH FRACTIONATION

| EXPERIMENT NUMBER | HEAT TREATED | IMC* | AMC* |
|---|---|---|---|
| 1A | No | 10 | 150 |
| 1B | No | 15 | 80 |
| 2A | Yes | 5 | 15 |
| 2B | Yes | 10 | 15 |

*IMC: initial molten color.
*AMC: aged molten color.

Without pretreatment, the aged molten color of the product obtained was outside the specification of 40 APHA maximum. With the heat soak step including 0.1% sulfuric acid the product was well within specifications.

EXAMPLE 2

Similar results as shown in Example 1 were obtained in a continuous fractionation thereby more closely duplicating commercial conditions. The feed was similar to that of Example 1. The heat soak was done batchwise for 20 hours at 150° C. in the presence of 0.1% sulfuric acid. The fractionator was operated for five hours continuously in each experiment under similar conditions. The molten color determinations in TABLE II are averages of ten tests.

TABLE II $H_2SO_4$ AS HEAT SOAK ADDITIVE IN CONTINUOUS FRACTIONATION

| RUN # | HEAT SOAK | IMC | AMC |
|---|---|---|---|
| 1 | No | 17 | 72 |
| 2 | Yes | 15 | 24 |

EXAMPLE 3

In this series of experiments sulfuric acid, hydrogen peroxide and a combination of both are found to be effective heat soak additives for maleic anhydride. Again commercially produced impure maleic anhydride from butane oxidation is used. The heat treatment is conducted for 24 hours at a temperature of 148.5° C. Thereafter batchwise fractionation under the conditions used in Example 1 is conducted. The addition agents, their concentration of use and the aged molten color (AMC) of the maleic acid product fraction are shown in TABLE III to follow.

TABLE III

ADDITIVE EFFECT ON AGED MOLTEN COLOR OF PRODUCT MALEIC ANHYDRIDE

| Additive, Concentration | AMC |
|---|---|
| No Heat Treatment | 125, 150* |
| Heat Treatment but No Additive | 80 |
| Hydrogen Peroxide, 0.03 weight percent | 40 |
| Sulfuric Acid, 0.1 weight percent | 30 |
| Sulfuric Acid, 0.1 wt. % and $H_2O_2$, 0.03 wt. % | 20, 20* |

*Results of duplicate experiments.

The foregoing are intended only to illustrate the understanding and practice of the present invention and are not intended as a limitation thereon. Rather the scope of the present invention is limited only by the claims to follow.

The invention claimed is:

1. A method of improving the aged molten color of maleic anhydride product obtained by the oxidation of butane vapor with air which comprises heating the impure maleic anhydride to a temperature in the range of from 60° C. up to 202° C. in the presence of from 0 up to 0.2 weight percent sulfuric acid and from 0 up to 0.1 weight percent hydrogen peroxide as an addition agent for up to 48 hours prior to fractionation of impure maleic anhydride to obtain the maleic acid product fraction.

2. The method of claim 1 wherein the addition agent is 0.1 weight percent sulfuric acid and the mixture of impure maleic anhydride and sulfuric acid is maintained at a temperature of 150° C. for 24 hours.

3. The method of claim 1 wherein the addition agent is 0.03 weight percent hydrogen peroxide and the mixture thereof with maleic anhydride is maintained at 150° C. for 24 hours.

4. The method of claim 1 wherein the addition agent is 0.1 weight percent sulfuric acid and 0.03 weight percent hydrogen peroxide and the mixture thereof with impure maleic anhydride is maintained at 150° C. for 24 urs.

* * * * *

UNITED STATES PATENT AND TRADEMARK OFFICE
CERTIFICATE OF CORRECTION

PATENT NO. : 4,260,546

DATED : April 7, 1981

INVENTOR(S) : Hobe Schroeder et al.

It is certified that error appears in the above—identified patent and that said Letters Patent is hereby corrected as shown below:

Column 3, line 24, "heart" should read --- heat ---.

Column 4, line 61, "urs." should read --- hrs. ---.

Signed and Sealed this

Eleventh Day of August 1981

[SEAL]

Attest:

GERALD J. MOSSINGHOFF

Attesting Officer　　Commissioner of Patents and Trademarks